United States Patent
Thangaraj et al.

(10) Patent No.: US 8,540,895 B2
(45) Date of Patent: Sep. 24, 2013

(54) SOLID COMPOSITIONS AND METHODS FOR GENERATING CHLORINE DIOXIDE

(75) Inventors: John Appadurai Thangaraj, Edison, NJ (US); Lakkaraju Dasaradhi, Princeton Junction, NJ (US)

(73) Assignee: Sipka Inc., Edison, NJ (US)

( * ) Notice: Subject to any disclaimer, the term of this patent is extended or adjusted under 35 U.S.C. 154(b) by 68 days.

(21) Appl. No.: 13/177,275

(22) Filed: Jul. 6, 2011

(65) Prior Publication Data

US 2011/0309297 A1 Dec. 22, 2011

Related U.S. Application Data

(63) Continuation-in-part of application No. 11/854,434, filed on Sep. 12, 2007, now abandoned.

(60) Provisional application No. 60/825,718, filed on Sep. 15, 2006.

(51) Int. Cl.
*C01B 11/10* (2006.01)
*C01B 11/02* (2006.01)
*C09K 3/00* (2006.01)

(52) U.S. Cl.
USPC ............ 252/187.23; 252/187.21; 252/186.25; 252/186.36; 252/187.1

(58) Field of Classification Search
USPC ............................ 252/187.23, 187.21, 186.25
See application file for complete search history.

(56) References Cited

U.S. PATENT DOCUMENTS

| | | | | |
|---|---|---|---|---|
| 4,104,190 | A * | 8/1978 | Hartshorn | 252/187.21 |
| 4,830,773 | A * | 5/1989 | Olson | 252/186.35 |
| 5,197,636 | A * | 3/1993 | Mitchell et al. | 222/190 |
| 5,336,434 | A * | 8/1994 | Park et al. | 252/187.21 |
| 5,338,480 | A * | 8/1994 | Dziabo et al. | 252/187.21 |
| 5,719,100 | A * | 2/1998 | Zahradnik et al. | 502/417 |
| 6,238,643 | B1 * | 5/2001 | Thangaraj et al. | 423/477 |
| 6,663,902 | B1 * | 12/2003 | Hei et al. | 424/661 |
| 6,699,404 | B2 * | 3/2004 | Speronello et al. | 252/187.23 |
| 6,921,743 | B2 * | 7/2005 | Scheper et al. | 510/220 |
| 7,465,410 | B2 * | 12/2008 | Martin et al. | 252/186.25 |
| 2006/0169949 | A1 * | 8/2006 | Speronello et al. | 252/187.23 |
| 2007/0172412 | A1 * | 7/2007 | Hratko et al. | 423/477 |
| 2007/0202095 | A1 * | 8/2007 | Speronello et al. | 424/126 |
| 2008/0067470 | A1 * | 3/2008 | Thangaraj et al. | 252/187.21 |
| 2011/0150748 | A1 * | 6/2011 | Thangaraj | 423/477 |

* cited by examiner

*Primary Examiner* — Joseph D Anthony
(74) *Attorney, Agent, or Firm* — Smyrski Law Group, A P.C.

(57) ABSTRACT

A composition for generating chlorine dioxide comprises active ingredients, a suitable hydrophobic compound, and a suitable super absorbent compound. A suitable hydrophobic compound will, among other characteristics, repel the solvent for at least the initial 30 seconds of exposure thereto. A suitable super absorbent compound will, among other characteristics, absorb at least 75 times its weight in solvent and will not gel until the chlorine-dioxide generating reaction is substantially complete.

20 Claims, No Drawings

SOLID COMPOSITIONS AND METHODS FOR GENERATING CHLORINE DIOXIDE

STATEMENT OF RELATED CASES

This case is a continuation-in-part of U.S. patent application Ser. No. 11/854,434, which is incorporated herein by reference.

FIELD OF THE INVENTION

The present invention relates generally to the chlorine dioxide, and more particularly to methods and solid compositions for generating chlorine dioxide.

BACKGROUND OF THE INVENTION

Chlorine dioxide ($ClO_2$) is a highly reactive yellowish-green gas molecule. Highly soluble in water, $ClO_2$ is used in a variety of applications, such as for pulp-bleaching, as a bactericide, a viricide, an algaecide, a fungicide, a potent antimicrobial agent and a selective oxidizer. Chlorine dioxide is an effective antimicrobial even at very low concentrations and over wide range of pH.

A variety of methods are known for generating chlorine dioxide. It is typically produced commercially from aqueous solutions of chlorite-containing salts. See, e.g., U.S. Pat. No. 5,009,875 and Ullmann's Encyclopedia of Industrial Chemistry, vol. A 6, p. 496-500.

The reaction by which sodium chlorite and acid generate chlorine dioxide is exceedingly vigorous at high concentrations of reactants. If the reaction rate is not controlled, explosion can result, since chlorine dioxide is explosive in gaseous concentrations of about 10 volume percent in air. Due to its explosive nature and inherent instability, chlorine dioxide is generally not transported; it has historically been produced on-site at the time of use.

The focus of most recent efforts in chlorine-dioxide generation has been toward the creation of stable formulations and solutions. That is, precursor formulations that have a non-trivial shelf life and solutions of chlorine dioxide that, once formed, persist for weeks.

One such approach is to provide "stabilized" chlorine dioxide products. These products release chlorine dioxide, thereby creating a solution of "free" chlorine dioxide, when the pH is lowered to provide an acidic environment. See, for example, U.S. Pat. Nos. 3,123,521, 3,147,124, 4,396,102, 5,324,447 and 5,336,434.

The latter two patents referenced above, U.S. Pat. No. 5,324,447 and U.S. Pat. No. 5,336,434, disclose systems for cleaning contact lenses. U.S. Pat. No. 5,324,447 discloses a two-part chlorine-dioxide releasing system, wherein one part is a tablet activator and the other is a stabilized chloride dioxide product. This product is available from Bio-cide International Inc. under the trademark PUREGENE®. U.S. Pat. No. 5,336,434 also discloses a two-part chorine-dioxide releasing system wherein one part is the stabilized sodium chloride dioxide (i.e., PUREGENE®) and the other part (the activator) is a tablet consists of a reducing agent (i.e., sodium thiosulfate). Dropping the activator tablet into the stabilized chlorine dioxide solution generates free chlorine dioxide via a reducing mechanism. No extra acid is added, thereby avoiding a pH change. The activator tablet also includes an enzyme for removing certain debris from a contact lens. Because many enzymes are inactive in the presence of chlorine dioxide, the release of the activator (reducing) component is delayed via a delayed release component, such as certain cellulose compounds.

U.S. Pat. No. 7,229,647 discloses storing pre-generated chlorine dioxide in sodium/potassium polyacrylic acid water-absorbent polymer.

Another common approach for chlorine-dioxide generation is to prepare compositions comprising dry pre-mixed solid ingredients, wherein the reaction is activated by water vapor or liquid water. As previously indicated, if the composition contains an alkali metal chlorite salt (e.g., sodium chlorite, etc.) and acid, it will react violently, even when exposed to a relatively small amount of water vapor or liquid water. As a consequence, preparations that are activated by water must control the supply of water to the solid reactants. This is often done using some type of physical barrier.

U.S. Pat. No. 5,719,100, for example, discloses the production of chlorine dioxide in an aqueous solution from a tablet comprising a composition of sodium chlorite and an acid activator, wherein the composition requires a coating that segregates the sodium chlorite and acid component. U.S. Pat. No. 6,238,643 discloses separating the reactants—a metal chlorite and an acid-forming component—from liquid water by a membrane (i.e., a Tyvek® bag/sachet). The membrane permits controlled passage of liquid water and/or water vapor. Chlorine dioxide is generated when water passes through the membrane. The chlorine dioxide that is generated passes out through the membrane into liquid water to produce the desired aqueous chlorine dioxide solution.

Another approach for controlling the reaction rate is to segregate reactants in a shell or compartmentalized structure and use a wick, etc., to control the rate at which the reactants are brought into contact with one another. For example, U.S. Pat. No. 5,091,107 discloses bringing an aqueous chlorite composition into contact, at a controlled rate via a wick, etc., with an absorbent pad containing acid or other reactant that will react with the chlorite to form chlorine dioxide. Similarly, U.S. Pat. No. 6,764,661 discloses a membrane shell that defines a compartment. The compartment includes reactants that generate chlorine dioxide gas when exposed to water. A wick extends into the compartment for absorbing water and transporting water into the compartment so that the chemical(s) in the compartment dissolve in the water and produce chlorine dioxide. U.S. Publ. Pat. Application 2009/0142235 discloses a disinfectant-generating device that includes a membrane shell defining at least two compartments. Each of the compartments includes at least one dry reactant capable of reacting and producing a disinfectant upon exposure of the device to water or ambient moisture. Each compartment is provided with an outer membrane defining walls of the device, an inner membrane providing physical separation of the dry reactants, and a wick.

U.S. Pat. Nos. 5,974,810, 6,077,495, 6,294,108, 7,220,367 disclose methods, compositions and systems for generating chlorine dioxide gas in a controlled-release manner.

A further and popular approach to generating chlorine dioxide is to include a free halogen (chlorine) source, such as sodium dichloroisocyanuric acid (NaDCC), in the composition. When exposed to water, the composition releases chlorine dioxide. See, e.g., U.S. Pat. Nos. 4,104,190, 6,432,322, 6,699,404, 7,182,883, 7,465,410, and U.S. Publ. Pat. Appls. 2006/0169949 and 2007/0172412.

An additional method for the controlled generation of chlorine dioxide is disclosed in U.S. Pat. No. 6,921,743, wherein chlorine dioxide is generated electrochemically; an acid activator is not required.

The prior-art devices and methods discussed above suffer from a variety of drawbacks. For methods that use a sachet/bag to generate chlorine dioxide, when the bag is placed in water, chlorine dioxide is generated at a rate that is often greater than the rate at which it permeates out of the sachet. As a consequence, a high concentration of $ClO_2$ gas can result inside the sachet, resulting in explosion.

Prior art devices and methods that use membranes are susceptible to premature activation by water or water vapor. This results in a reduced shelf life unless sufficient steps, such as providing an air-tight foil seal, are taken to prevent exposure to ambient moisture or water. But even when such a seal is used, after a few months of storage, the foils tend to crack and lose their seal.

Many of the prior-art compositions include calcium or magnesium salts as a desiccant to preserve self life. In the absence of these salts, premature release of chlorine dioxide typically occurs, which can result in explosion. If the chlorine dioxide is intended for use in a soapy solution, the presence of these salts is detrimental because they add hardness to the water. Furthermore, due to the heat of hydration, the presence of calcium or magnesium salts undesirably adds more heat to the already quite exothermic chlorine-dioxide-generating reaction between sodium chlorite and acid.

Tablets generally produce chlorine dioxide at a greater rate than membrane devices because the tablet does not have a membrane to restrict chlorine dioxide from escaping into solution. But the quality of the resulting $ClO_2$ is questionable because unconverted reagents are present along with the $ClO_2$. As previously discussed, many compositions include the free-chlorine source sodium dichloroisocyanuric acid (NaDCC) for generating chlorine dioxide. Such compositions generate little or no chlorine dioxide in the absence of NaDCC. But for many applications, the presence of NaDCC with the generated $ClO_2$ is undesirable.

A need therefore remains for a simple, convenient, and safe way to generate chlorine dioxide gas or solutions at high yield and with high quality, and from a composition that has a long shelf life.

SUMMARY OF THE INVENTION

The present invention provides compositions and methods to generate chlorine dioxide that avoid many of the drawbacks and costs of the prior art. At least some embodiments of the compositions and methods disclosed herein exhibit one or more of the following characteristics:
  enable chlorine dioxide to be generated quickly and without explosion;
  enable chlorine dioxide to be generated in a suitable quantity for a variety of different disinfecting/sanitizing applications;
  enable a considerable quantity of chlorine dioxide to be generated in the absence of a free-chlorine source;
  possess long shelf life in the absence of calcium salts or magnesium salts; and
  generate considerable quantities of chlorine dioxide regardless of form (i.e., a loose powder that is sprinkled into water, a powder retained in a canister or sachet, etc., or a tablet).

A chlorine-dioxide-generating ("CDG") composition in accordance with the illustrative embodiment of the present invention comprises (a) active ingredients and (b) required inert ingredients. The CDG composition generates chlorine dioxide when exposed to a liquid solvent, typically water or alcohol. The CDG composition can also generate chlorine dioxide when exposed to high levels of moisture in air, etc., but that is typically an undesired consequence.

The "active ingredients" of the CDG composition are the compounds that react to form chlorine dioxide. Typical active ingredients include an alkali metal chlorite salt and a solid acid.

The required inert ingredients, although multifunctional, are used primarily to control the access of solvent to the active ingredients for a relatively brief period of time. Typical solvent-control ingredients include specific hydrophobic cellulosic materials and specific "super" absorbents. In some embodiments, CDG compositions in accordance with the present invention also include optional inert ingredients, such as, without limitation, surfactants (for forming a soapy solution of chlorine dioxide), fillers, disintegrates (for tablet formations), etc.

The inventor's familiarity with existing chlorine-dioxide generating compositions and products—and their shortcomings—provided direction for the development of the present invention. The following goals and objectives were of importance:
  Devise a simple way to control the access of water to the active ingredients of the CDG composition.
  The CDG composition should comprise common, readily available chemicals and should be formed via a simple process that is amenable to commercial-scale implementation.
  Safely generate chlorine dioxide irrespective of the amount (weight) of the CDG composition.
  Generate chlorine dioxide without "booster" chemicals, such as a free-halogen source.
  Avoid the use of Ca and Mg desiccant salts.
  Provide a long shelf life (>1 year).
  Develop a CDG composition that generates a substantial yield of chlorine dioxide regardless of the form of the composition—a tablet, a capsule, or a powder for (i) adding directly to water or (ii) for use in a porous housing, sachet, etc.

In CDG compositions in accordance with present invention, as in many prior-art CDG compositions, the ingredients are dried. As a consequence, the ingredients tend to absorb solvent (e.g., water, etc.) rapidly, although much faster upon initial exposure than with continued exposure. The rate of the chlorine-dioxide-generating reaction (alkali metal chlorite salt+acid) is controlled by the water (or alcohol). As a consequence, if contact with the solvent is not controlled during this initial exposure, the chlorine-dioxide-generating reaction is uncontrolled, which can lead to explosion. It is therefore critical to control the access of solvent to the active ingredients during the first few minutes of the reaction.

To satisfy some or all of the goals listed above, CDG compositions in accordance with the present invention control access to water, but do so differently than the prior art. Rather than using coating or encapsulating materials to separate reactants, or compartmentalized structures with wicks, etc., embodiments of the present invention use a multi-compound, multi-stage, physicochemical approach to water control.

More particularly, in the accordance with the illustrative embodiment, a first stage of control is provided by a hydrophobic compound that repels solvent. A second stage of control is provided by a super absorbent that absorbs solvent. This multi-stage, multi-compound approach effectively limits the availability of the solvent to the active ingredients for a brief, but nevertheless very important period of time.

The inventor discovered that when a CDG composition is placed in solvent, such as water, the reaction can be moderated by the hydrophobic compound for at least the initial 30 to 120 seconds. A super absorbent will take at least about 30 to 60 seconds to absorb water and is therefore relatively ineffective during this initial period of time. But after the initial period, solvent that gets past the hydrophobic compound (and that is in excess of what is required to complete the chlorine-dioxide generating reaction) is rapidly absorbed by the super absorbent. This "absorption" phase of the method reduces excess solvent, which would otherwise (1) reduce the yield of chlorine dioxide and (2) result in a violent reaction. In this fashion, the initial exposure of the active ingredients to solvent is moderated. After this initial period, the hydrophobic compound and the super absorbent are of decreased importance since the active ingredients are partially saturated with solvent and tend to absorb additional solvent at a relatively reduced rate.

As discussed more fully in the following Detailed Description, laboratory testing has revealed that both of the solvent-control components—the hydrophobic compound as well as the super absorbent—are required for a CDG composition that is safe (substantially no likelihood of explosion for quantities of up to at least 200 grams) and has a shelf life of at least one year (more typically three or more years). And testing has also revealed that not all hydrophobic compounds, nor all super absorbents, are capable of so performing.

CDG compositions in accordance with the present teaching generate chlorine dioxide in an amount up to about 10 percent by weight of the CDG composition without adding a free chlorine source or other reducing chemicals. This is in contrast to many prior-art CDG compositions, which generate virtually no chlorine dioxide without the presence of a free chlorine source. Moreover, to the inventor's knowledge, no prior-art CDG composition in the form of loose powder, when placed in water, generates anything more than a trivial and application-insufficient amount of chlorine dioxide in the absence of a free chlorine source. Some CDG compositions in accordance with the present invention that exclude a free chlorine source, however, generate a large amount of chlorine dioxide (up to about 5 percent by weight) when loose powder is sprinkled directly into solvent. Additionally, due to the presence of the super absorbent, the CDG composition does not require magnesium or calcium salts for use as a desiccant to achieve a long shelf life. Some CDG compositions in accordance with the present teachings have achieved a shelf life in excess of 3 years in the absence of such salts.

In some embodiments, the hydrophobic compound is an appropriately selected hydroxypropyl methylcellulose ("HPMC") compound and the super absorbent is an appropriately selected sodium polyacrylate. And to achieve specific performance levels, such as chlorine dioxide yield, shelf life, etc., or even avoid explosion, the concentration of such compounds is an important consideration.

It is notable that not all hydrophobic compounds, nor even all versions of HPMC, are appropriate or otherwise desirable for use in all CDG compositions disclosed herein. Likewise, not all super absorbents, nor even all sodium polyacrylates, are appropriate or otherwise desirable for use in all CDG compositions disclosed herein. Only those hydrophobic compounds that exhibit an acceptable level of hydrophobicity, a desired solubility, a desired viscosity, etc., are suitable for use in the inventive CDG compositions. And only those super absorbents that exhibit a desired gelation time, molecular weight, solvent-absorption capacity, etc., are suitable for use in the inventive CDG compositions.

In this regard, it is notable that the prior art CDG compositions have included both HPMC and sodium polyacrylate. In particular, HPMC has been used as a binder and as a coating agent for extended-release compositions. As discussed further in the Detailed Description, there are various types of HPMC having different characteristics. The characteristics that are required or otherwise desirable for repelling water, in accordance with embodiments of the invention, might not be present when simply selecting HPMC for use as a binder or extended-release coating as in the prior art. Furthermore, it is notable that providing an extended-release version of a CDG composition is not equivalent to restricting the access of solvent to the active ingredients of the CDG composition. That is, if a CDG composition that includes dried alkali metal chlorite salt and a dry solid acid is released over time, explosion can still occur because once those active ingredients are exposed to solvent, rapid absorption and uncontrolled reaction results.

Likewise, sodium polyacrylate has been used in the prior art, typically at high concentrations, as a thickener. But as discussed more fully in the following Detailed Description, the presence of sodium polyacrylate can lead to explosion if the polyacrylate is not selected to provide a specific minimum gelation time. Furthermore, at increasing levels of concentration, it has been determine that the presence of sodium polyacrylate in CDG compositions, especially those that do not include a free chorine source, has a significant adverse affect on chlorine dioxide yield.

It is only with appropriately selected hydrophobic and super absorbent compounds at suitable concentrations that safe release and high yield of chlorine dioxide as well as long shelf life of the CDG composition is realized. The Detailed Description provides a more extensive listing of suitable hydrophobic compounds and super absorbents and desired characteristics thereof.

The hydrophobic compound and the super absorbent provide other "minor" functions in conjunction with the CDG compositions disclosed herein. For example, HPMC also serves as a diluent to separate the active ingredients to avoid premature release of chlorine dioxide. In that regard, as used in some embodiments of the present invention, the hydrophobic compound is usually in the form of a dust that "sticks" to the active ingredients. The hydrophobic compound can also function as a binder for pressing tablets and to slow the rate of disintegration of tablets. And sodium polyacrylate also functions as an acid pump whereby it controls acid concentration by absorbing/exchanging acid, as a desiccant, and as a thickener for soap.

Unlike some prior-art CDG compositions (see, e.g., U.S. Pat. No. 7,465,410), some embodiments of CDG compositions disclosed herein do not use any coating whatsoever on the active ingredients (e.g., sodium chlorite and solid acid, etc.) once they are combined. When using a CDG composition that generates chlorine dioxide via the reaction of an alkali metal chlorite salt and an acid as described herein, chlorine dioxide will be released if the active ingredients are subjected to the coating process (due to the aerosol or spray components). This is to be avoided.

CDG compositions in accordance with the present teachings preferably comprise:

Alkali metal chlorite salt: about 2 to about 35 weight pct of the CDG composition;

Acid: about 2 to about 45 weight pct of the CDG composition;

Hydrophobic compound: about 2 to about 20 weight pct of the CDG composition;

Super absorbent: about 2 to about 15 weight pct of the CDG composition; and

Optional inert ingredients: balance.

The concentration ranges listed above break-down into "more-preferred" ranges as a function, for example, of application specifics. Chlorine-dioxide yield, for example, will vary with application specifics and the concentration of the active ingredients can vary with the desired chlorine-dioxide yield. Both the type and concentration of the hydrophobic compound and the super absorbent can vary as a function of the amount (weight) of the CDG sample and the concentration of active ingredients. Further discussion related to more-preferred ranges of compounds in the CDG composition, as well as many other relevant considerations, are provided in the following Detailed Description.

CDG compositions in accordance with the present teachings will further be characterized by any one or more of the following characteristics:

(i) Will exclude a free chlorine source (e.g., sodium dichloroisocyanuric acid, etc.).
(ii) Will exclude calcium or magnesium salts.
(iii) The gelation time for the super absorbent is at least 5 minutes.
(iv) The gelation time for the super absorbent is at least 10 minutes.
(v) The gelation time for the super absorbent is at least 30 minutes.
(vi) The hydrophobic compound is a hydroxypropyl methylcellulose available from Dow Chemical Company under the tradename METHOCEL™, wherein the METHOCEL™ is selected from the group consisting of METHOCEL E15, METHOCEL E17, METHOCEL E19, METHOCEL H, METHOCEL J, METHOCEL K100 M, and METHOCEL 310 series.
(vii) The hydrophobic compound is a hydroxypropyl cellulose available from Ashland Chemical Company under the tradename KLUCEL™, wherein the KLUCEL™ is selected from the group consisting of KLUCEL E and KLUCEL G.
(viii) The hydrophobic compound contains hydroxypropyl groups in an amount greater than 5 percent by weight of the hydrophobic compound.
(ix) The super absorbent is sodium polyacrylate having a weight average molecular weight of at least 5000 grams/mol.
(x) The super absorbent is sodium polyacrylate having a weight average molecular weight of at least 70,000 grams/mol.
(xi) The super absorbent is sodium polyacrylate having a weight average molecular weight of between about 125,000 to about 250,000 grams/mol.
(xii) The super absorbent is a sodium salt of polyacrylic acid.
(xiii) More hydrophobic compound is present than super absorbent (by weight).
(xiv) The super absorbent compound is present in a given CDG composition at a maximum amount that reduces chlorine dioxide yield by no more than about 20 percent from the maximum yield attained for that CDG composition, which maximum yield will be attained at some of amount of super absorbent that is less than that maximum amount.
(xv) The optional inert ingredients comprise a surfactant that does not react with chlorine dioxide or substantially impede its yield or release.
(xvi) The active ingredients, once mixed, are not coated.
(xvii) The active ingredients, hydrophobic compound, and super absorbent have an average particle size within the range of 50 mesh to 10 mesh.

DETAILED DESCRIPTION

Definitions

The following terms are defined for use in this specification, including the appended claims:

"Super absorbent compound" is a compound that absorbs at least seventy-five times its weight in solvent.

"Molecular weight" when used to describe polymer molecular weight, means weight average molecular weight.

"High molecular weight," when used to modify a compound (e.g., high molecular weight sodium polyacrylate, etc.) means a super absorbent form of the compound.

Additional definitions are provided elsewhere in the Detailed Description in context.

In accordance with the illustrative embodiment of the present invention, a chlorine-dioxide-generating ("CDG") composition in a dry powered form generates chlorine dioxide on exposure to a solvent. The solvent can be, without limitation, water vapor, wet air, liquid water, or alcohols (e.g., ethanol, isopropyl alcohol, etc.). The chlorine dioxide can be released into the atmosphere for gas-phase treatment applications or into solvent for liquid-phase treatment applications.

CDG Composition.

The CDG composition comprises:
(a) active ingredients (compounds that react to form chlorine dioxide);
(b) required inert ingredients (compounds that do not participate in the reaction, but are nevertheless required); and
(c) optional inert ingredients (compounds that might or might not be present as a function of application specifics).

The active ingredients include an alkali metal chlorite salt (or the less common alkaline metal chlorite salt) and an anhydrous solid acid. In the illustrative embodiment, sodium chlorite is oxidized by the acid to form chlorine dioxide as follows:

$$NaClO_2 + H^+ \rightarrow ClO_2 \qquad [1]$$

Suitable alkali metal chlorite salts include, without limitation, sodium chlorite, potassium chlorite, and lithium chlorite.

Suitable solid acids include, without limitation, citric acid, mono and di-sodium citrate, sodium hydrogen sulfate, sodium di-hydrogen and mono-hydrogen phosphates, tetra-sodium etidronate (tetra-sodium (1-hydroxyethylidene) bis-phosphates, poly(acrylic acid) partial sodium salt, poly (acrylic acid) partial potassium salt, and acid-impregnated inorganic solids.

The required inert ingredients are necessary, in accordance with the present teachings, to control access of the solvent to the active ingredients. The required inert ingredients include a "hydrophobic compound" and a "super absorbent." Notwithstanding any conventional usage, these terms are explicitly defined for use in this specification, including the appended claims. The definition of "super absorbent" has already been provided; the definition of "hydrophobic compound" follows below.

Suitable hydrophobic compounds include certain preparations of hydroxypropyl methylcellulose ("HPMC"), such as some of those available from Dow Chemical Company under the tradename METHOCEL™. There are a variety of versions of METHOCEL™; versions suitable for use in conjunction with embodiments of the invention include, without limitation, METHOCEL E15, METHOCEL E17, METHOCEL E19, METHOCEL H, METHOCEL J, METHOCEL K100 M, and METHOCEL 310 series.

An additional suitable hydrophobic compound includes hydroxypropyl cellulose available from Ashland Chemical Company under the tradename KLUCEL™. There are a variety of "versions" of KLUCEL™; versions suitable for use in conjunction with embodiments of the invention include, without limitation, KLUCEL E AND KLUCEL G.

Additional potentially suitable hydrophobic compounds include, without limitation, methyl cellulose, ethyl cellulose, propyl cellulose, hydroxymethyl cellulose, and microcrystalline cellulose. As discussed further below, the suitability of these particular hydrophobic compounds depends upon other characteristics of the CDG composition, such as, for example, the weight of the CDG composition and/or the concentration of the active ingredients. More particularly, hydrophobic compounds such as methyl cellulose and ethyl cellulose will only be suitable, and not in all cases, when the quantity of the CDG composition and/or concentration of the active ingredients is quite low (e.g., 2 grams of CDG composition, etc.).

The hydrophobic compound, whether HPMC or any other potentially suitable compound, must possess certain characteristics and will desirably possess additional characteristics for use in conjunction with embodiments of the invention. In particular, in the context of the CDG compositions disclosed herein, a "hydrophobic compound" is defined for use in this specification, including the appended claims, as a compound that is suitably hydrophobic to repel solvent (i.e., the solvent in which the chlorine dioxide will be released) for at least 30 seconds and is therefore able to prevent uncontrolled reaction/explosion for that period of time.

For example, certain versions of METHOCEL™ are less hydrophobic than others, and, depending upon the quantity of CDG composition present or the concentration of active ingredients, might or might not be suitable. Generally, the longer the carbon chain attached to the cellulose, the greater the hydrophobicity and the more desirable for use in conjunction with embodiments of the present invention. For example, propyl cellulose is more hydrophobic than ethyl cellulose, which, in turn, is more hydrophobic than methyl cellulose.

In compounds such as HPMC and hydroxypropyl cellulose, it is desirable to have a relatively greater number of propyl groups because that is associated with increased hydrophobicity and increased solubility in water. If the CDG composition is sprinkled into the solvent (typically water) as a loose powered form or in tablet form, the CDG composition must be soluble in the solvent. In this regard, it is desirable that the HPMC completely solubilizes in the solvent within 5 to 20 minutes to form a clear solution. If, however, the CDG composition is retained in a porous container, etc., there is no need for it to solubilize into the solvent.

Although certain hydrophobic compounds will be suitable for some applications, they will not be suitable for all applications. As previously noted, in applications that use a small quantity of CDG composition, such as 2 grams, it might be acceptable to use methyl or ethyl cellulose. But at quantities in excess of a few grams, such compounds are likely to be inadequately hydrophobic to repel solvent for the necessary amount of time to prevent explosion. In such cases, a propyl-substituted cellulose is desirable, such as versions of METHOCEL™, hydroxypropyl cellulose, etc.

For CDG compositions that are intended to completely solubilize, a relatively low viscosity and high solubility are desired. In such cases, if a version of HPMC is used as the hydrophobic compound, its molecular weight will typically be in the range of about 5000 to 10,000. Relatively lower molecular-weight species of HPMC will have relatively lower viscosity and higher solubility than relatively higher molecular-weight species of HPMC. For CDG compositions that include HPMC and are intended for use in canisters (and need not solubilize), a relatively high-viscosity form of HPMC is acceptable. The molecular weight of such HPMC will typically be greater than about 50,000.

Ultimately, routine laboratory testing will verify the suitability (or unsuitability) of any particular hydrophobic compound in the context of any specific CDG composition (e.g., amount and compositional breakdown, etc.).

Super absorbent compounds suitable for use in conjunction with the present invention exhibit the following characteristics:
  (1) a very high solvent-absorbing capability (at least 75× and more preferably 100× its weight in solvent);
  (2) an appropriately slow solvent-release property;
  (3) not reactive with the active ingredients; and
  (4) a suitable gelation time.

Suitable super absorbent compounds include, without limitation, crosslinked polyacrylic acid salts, crosslinked isobutylene-maleic acid copolymer derivatives, crosslinked starch-polyacrylic acid salts, crosslinked polyvinyl alcohol-polyacrylic acid salts, cross-linked polyvinyl alcohol derivatives, crosslinked polyethylene glycol derivatives and crosslinked carboxymethylcellulose derivatives. Some additional super absorbents include certain starch super-absorbent polymers having a molecular weight of at least about 500 grams/mol, and clays, such as inorganic Pillard clays, and silica.

A particularly preferred super absorbent compound is sodium polyacrylate. Sodium polyacrylate used in conjunction with a CDG composition in accordance with the present teachings will have a molecular weight in the range of about 5000 to 10,000,000 g/mol, depending on application specifics. If, for example, the application requires generating chlorine dioxide very quickly (the reaction is complete in about 5 minutes or less) and further requires forming a clear solution in the solvent very quickly (within about 5 minutes or less), then the molecular weight of the sodium polyacrylate should be toward the lower end of the specified range (i.e., about 5,000 to about 10,000 grams/mol). More typically, sodium polyacrylate having a molecular weight above 70,000 grams/mol is preferred, and even more preferable is sodium polyacrylate having a molecular weight within a range of about 125,000 to about 250,000 grams/mol.

Another particularly preferred super absorbent compound is sodium polyacrylamide having a molecular weight of at least 400. Also preferred are sodium salts of polyacrylic acid, such as polyacrylic acid partial sodium salt and polyacrylic acid partial sodium salt-graft-poly(ethylene oxide), wherein (solvent absorption increases as more acid groups are exchanged with sodium). Additional super absorbents include potassium polyacrylate and polyacrylic acid partial potassium salt.

It will be recognized by those skilled in the art that not all forms of the compounds listed above as "super" absorbent will, in fact, be "super absorbent" as defined herein. In particular, low-molecular-weight forms of the compounds will not be super absorbent. Only high-molecular weight forms of the compounds are "super" absorbent. Furthermore, it will be understood that not all super absorbent compounds (i.e., compounds absorbing at least 75× their weight in solvent) are suitable for use in conjunction with the present invention. Specifically, a "suitable" super absorbent compound must have an appropriately slow solvent-release property and not react with the active ingredients. For any given CDG composition, the rate of solvent release should be consistent with the time it takes for completion of the chlorine-dioxide reaction. That is, the super absorbent should hold substantially all of the solvent it absorbs until the reaction is substantially complete. For CDG compositions in accordance with the present teachings, the chlorine dioxide reaction will usually take from a minimum of about 5 minutes to a maximum of about 60 minutes to complete, as a function of composition specifics.

Super-absorbent polymers tend to form thick gel after adsorbing an amount of solvent. The gel traps the chlorine dioxide being generated, which can result in explosion. It is, therefore, critically important that the super absorbent compound selected for use in CDG compositions disclosed herein has a gelation time that is appropriate for the completion time of the chlorine-dioxide generating reaction. Specifically, the super absorbent should not gel before the chlorine-dioxide generating reaction is substantially complete. For example, if an application requires that the chlorine-dioxide generating reaction is complete within 5 minutes, then a super absorbent compound having a gelation time of about 5 minutes is acceptable. If, however, the CDG composition is such that the chlorine-dioxide generating reaction will take about 15 minutes for completion, then a super absorbent having a gelation time of at least about 15 minutes is required. If a super absorbent having a gelation time of 5 minutes were used in this latter case, an explosion would likely result.

Routine laboratory testing will confirm the suitability or lack thereof of any particular super absorbent compound (e.g., as to its solvent-release property, gelation time, and lack of reactivity with respect to the active ingredients, etc.) in the context of any specific CDG composition (e.g., amount and compositional breakdown, etc.).

In some embodiments, the CDG composition comprises one or more optional inert ingredients, such as surfactants, fillers, disintegrates (for tablet formations), and the like.

The presence of the surfactant results in the formation of a soapy chlorine-dioxide solution. Suitable surfactants include those that do not react with chlorine dioxide in the solid compositions disclosed herein because, for the most part, they do not react with chlorine dioxide or interfere with its release. Examples include, without limitation, SLS (sodium dodecyl sulfate or sodium laureth sulfate), alkyl sulfonates such as 1-pentane sulfonic acid sodium salt monohydrate, 1-hexane sulfonic acid sodium salt monohydrate, 1-heptane sulfonic acid sodium salt monohydrate, 1-octane sulfonic acid sodium salt, 1-decane sulfonic acid sodium salt, sodium dodecyl benzene sulfonate, linear alkyl benzene sulfonate, sodium alkyl naphthalene sulfonate.

Suitable non-ionic surfactants include alkyl poly (ethylene oxide), and more specifically polyethylene oxide. Cationic and zwitterionic surfactants are also suitable for use in conjunction with the illustrative embodiment of the present invention. Quaternary amine surfactants cannot be used because they react with chlorine dioxide.

Preferred and More-Preferred CDG Compositions

Typical applications for CDG compositions in accordance with the present invention will involve some number of small chlorine dioxide "generators" that include between about 2 grams to about 500 grams, and more typically between about 25 grams to about 100 grams of CDG composition. The number of generators used is a function of the size of the region or facility being treated and the required concentration of chlorine dioxide. The generator will include CDG compositions in accordance with the present teachings and will be in the form of a tablet, or loose powder sprinkled into solvent, or loose powder in a container, etc.

The selection of any particular CDG composition disclosed herein begins with the specifics of the application. The application will dictate or otherwise suggest:
  the form of the chlorine dioxide: "liquid" (i.e., in solution) or gaseous;
  if liquid, whether a surfactant should be included to generate a soapy solution;
  the manner of delivery (e.g., loose powder sprinkled in solvent, tablet dropped in solvent, powder in a sachet, pad, or, sack, powder in a container, etc.);
  the chlorine-dioxide release time (i.e., relatively quick or relatively slow); and
  the desired strength (i.e., concentration) of chlorine dioxide in solvent or in the volume for gaseous applications.

Typical "gaseous" applications include a relatively high concentration of chlorine dioxide—about 20 to about 1000 vppm—in non-occupied premises. For such applications, the CDG composition is tailored to provide a quick release of chlorine dioxide (e.g., about 2 to about 30 minutes for complete reaction). Treatment time is typically in the range of about 3 to 6 hours. Examples of such premises include, without limitation, a commercial food-production facility (sanitizing), a ballroom (mold/mildew) or guest rooms (mold/odor/bed bugs) of a hotel, grain silos (mold/bacteria), the basement of a private residence (mold/mildew/odor), automobiles (disinfect), cruise ship (mold/mildew), shipping containers (disinfect), commercial passenger vehicles (disinfect). Furthermore, chlorine dioxide gas generated via the CDG compositions disclosed herein can be used to treat surfaces, such as a counter top, laboratory hood, or surgical tools.

Typical "liquid" applications, with or without surfactants, will use a concentration of chlorine dioxide in the range of about 5 to about 3000 wppm in solvent, usually water. Example applications include cooling towers (algae control), oil wells (with or without surfactant), healthcare facilities (with or without surfactant), fruit/vegetable processing facilities (with or without surfactant), equipment/working-surface disinfection at food processing facilities (with or without surfactant), sanitizing food cutting boards, etc. (with surfactant).

For "liquid" applications in which humans are present during chlorine-dioxide generation and treatment, formulations that generate between about 5 to about 50 wppm of chlorine dioxide are preferred. Such applications include handwash soap, denture cleaning/mouthwash, foot/nail sanitizing SPA solutions, contact lens solutions, etc. In such applications, it is desirable to use a CDG composition that includes a relatively low concentration of active ingredients (e.g., 5 wt pct alkali metal chorite and 10 wt pct acid, etc.) so as to generate a relatively low yield of chlorine dioxide. It is less desirable to dilute a solution of having high levels of chlorine dioxide down to the desired range, such as would be necessary if a CDG composition that includes a relatively greater amount of active ingredients (e.g., 35 wt pct alkali metal chorite and 40 wt pct acid) were used.

After reading this disclosure, one skilled in the art will appreciate that any one or more of the following factors can be varied to generate a desired amount of chlorine dioxide:
  (i) the specific individual compounds used in the CDG composition;
  (ii) the concentrations of the specific individual compounds used in the CDG composition;
  (iii) the quantity of the CDG composition; and
  (iv) the delivery modality.

TABLE A. This table provides guidance as to the range of concentration (in weight percent) for the basic ingredients of CDG compositions disclosed herein. Various ranges for the ingredients are disclosed, defining "OK" (acceptable), "Pfd." (preferred), and "M-Pfd" (more preferred) CDG compositions. The ranges are based on laboratory testing, some of which is presented later in this specification in Tables 1-9.

TABLE A

CDG COMPOSITIONS: Acceptable, Preferred, and More Preferred

| Compound | CDG Composition | | | | | | |
|---|---|---|---|---|---|---|---|
| | OK | Pfd. | M-Pfd 5% | M-Pfd 10% | M-Pfd 20% | M-Pfd 25% | M-Pfd 35% |
| Alkali Metal Chlorite Salt | 2-80 | 2-35 | 5 −3/+3 | 10 −5/+5 | 20 −5/+5 | 25 −5/+5 | 35 −5/0 |
| Acid | 2-90 | 2-45 | 5 −3/+5 | 15 −5/+7 | 25 −5/+7 | 35 −5/+7 | 40 −5/+5 |
| Hydrophobic Compound | 2-60 | 2-20 | 5 −3/+5 | 5 0/+10 | 10 −5/+10 | 10 0/+10 | 15 −5/+5 |
| Super Absorbent Compound | 2-20 | 2-15 | 5 −3/0 | 5 −1/0 | 10 −5/0 | 10 −3/0 | 10 −3/0 |
| Optional Inerts | Bal. | Bal. | Bal. | Bal. | Bal. | Bal. | Bal. |

The guidance provided by Table A is generic in the sense that it must be evaluated in the context of application specifics, as previously indicated. In particular, a potentially acceptable "hydrophobic" compound might be more or less acceptable, or not acceptable at all, in the context of a particular application. The same is true for a specific choice of "super absorbent" compound. As previously discussed, parameters for consideration include, without limitation, the required amount of the CDG composition, delivery modality, and the particular selection of other compounds in the CDG composition.

The more-preferred CDG compositions listed above are referenced, for use in this specification including the appended claims, by the indicated nominal concentration of the alkali metal chlorite salt. For example, the "M-Pfd 5%" (more-preferred 5-percent) CDG composition is defined to comprise:
  an alkali metal chlorite salt with a nominal concentration of 5 weight percent, and ranging from about 2 weight percent (i.e., 5−3) to about 8 weight percent (i.e., 5+3);
  an acid source with a nominal concentration of 5 weight percent, and ranging from about 2 weight percent (i.e., 5−3) to about 10 weight percent (i.e., 5+5),
  a hydrophobic compound with a nominal concentration of 5 weight percent, and ranging from about 2 weight percent (i.e., 5−3) to about 10 weight percent (i.e., 5+5);
  a super absorbent compound with a nominal concentration of 5 weight percent, and ranging from about 2 weight percent (i.e., 5−3) to about 5 weight percent (i.e., 5+0); and
  optional inert components for the remainder of the composition.
The "M-Pfd 10% CDG composition", the "M-Pfd 20% CDG composition", "M-Pfd 25% CDG composition", and "M-Pfd 35% CDG composition" are similarly defined, as per the nominal concentration and allowable approximate range of concentration, as provided in Table A.

Notwithstanding the preferred and more preferred ranges provided in Table A for the "hydrophobic" compound, testing has indicated that there is little if any penalty for increasing the concentration of the hydrophobic compound to well beyond the listed ranges. For example, CDG compositions with relatively low levels of active ingredients (e.g., alkali metal chlorite salt at 5 weight percent and acid at 10 weight percent, etc.) have been prepared that have included in excess of 60 weight percent Methocel™ with seemingly no adverse affect on chlorine dioxide yield.

Preparation.

The CDG compositions disclosed herein are in the form of dry solid powders. The general procedure for forming the CDG compositions is:
  Granulate the alkali (or alkaline) metal chlorite salt to granular form or flakes having a size of about 1 to 2 millimeters. Other ingredients of the CDG composition typically have an appropriate size such that they can be used as is.
  Dry all ingredients at 105° C. for 2 to 3 hours.
  Bring the temperature of the ingredients to about 20° C. to 25° C. (i.e., room temperature).
  Dry blend the ingredients using a v-blender.
No special room conditions are required as long as relative humidity is below 60 percent.

The foregoing procedure produces a loose powder form of the CDG composition. If a tablet form of the CDG composition is desired, a conventional tableting machine is used. As will be appreciated by those skilled in the art, it is desirable to add certain excipients to the CDG composition, such as binders, disintegrants (e.g., polyvinyl pyrrolidone (PVP), poly plasodone cross povidone), lubricants, etc., to the extent a tablet is desired.

Examples

Testing has shown that a loose powder form of a CDG composition in accordance with the present invention will generate up to about 0.05 grams of chlorine dioxide per gram of CDG powder (5 weight percent yield). A tablet form of a CDG composition in accordance with the present invention will generate up to about 0.07 grams of chlorine dioxide per gram of CDG powder (7 weight percent yield). When a loose powder form of a CDG composition in accordance with the present invention is placed in a suitable canister, up to about 0.1 grams of chlorine dioxide per gram of CDG powder (10 weight percent yield) is generated.

During testing, most CDG compositions were first evaluated for safety (explosion) using porous poly-propylene containers of different sizes, as appropriate for the quantity of CDG composition being tested. CDG compositions tested ranged from 1 gram to 500 grams. In addition to producing the greatest yield, when using porous containers (or porous capsules, sachets, etc.), the residue of reacted salts and gels from the hydrophobic compound and the super absorbent remain within the container. As a consequence, the chlorine dioxide is generated with higher purity than when loose powder or a tablet is added directly to solvent.

For the following examples, analysis of chlorine dioxide in solvent was performed via HP 8453 UV spectrophotometer at 360 nm. Solution samples above 50 ppm were diluted to below 50 ppm to ensure they were accurately quantitated. Chlorine dioxide gas was analyzed using an Optex chlorine dioxide analyzer.

TABLE 1. This table shows the results of testing a 2-gram sample and a 5-gram sample of a first group of non-conforming CDG compositions.

TABLE 1

NON-CONFORMING CDG COMPOSITION: No Super Absorbent

| Hydrophobic Compound | \multicolumn{7}{c}{CDG Composition} | | | | | | |
|---|---|---|---|---|---|---|---|
| | 1 | 2 | 3 | 4 | 5 | 6 | 7 |
| Methyl Cellulose | X | X | 25 | X | X | X | X |
| Ethyl cellulose | X | X | X | 25 | X | X | X |
| (Methocel E15) | 25 | X | X | X | X | X | X |
| (Methocel E19) | X | 25 | X | X | X | X | X |
| (Methocel J) | X | X | X | X | 25 | X | X |
| (Methocel K100M) | X | X | X | X | X | 25 | X |
| (Klucel M) | X | X | X | X | X | X | 25 |
| Result at 2 grams | | | | | | | |
| ClO$_2$ (wppm) | 132 | 136 | — | — | 130 | 126 | 117 |
| Explosion | No | No | Yes | Yes | No | No | No |
| Result at 5 grams | | | | | | | |
| ClO$_2$ (wppm) | — | — | — | — | — | — | — |
| Explosion | Yes | Yes | Yes | Yes | Yes | Yes | Yes |

The CDG compositions in Table 1 included the requisite active ingredients (for these compositions: sodium chlorite was 35 wt pct and sodium hydrogen sulfate anhydrous was 40 wt pct). But of the required inert ingredients, only the hydrophobic compound was present (i.e., the super absorbent compound was absent). The testing of the 2 gram samples was conducted for 2 hours. The results provide the amount of chlorine dioxide generated (wppm) in 1-liter of water and whether or not there was an explosion.

The testing at 2 grams showed that with appropriately selected HPMC (the various Methocel™ formulations), the CDG composition was safe and produced a reasonable amount of chlorine dioxide. The shelf life of 2-gram samples of CDG compositions 1-7 was, however, quite short (a few days to less than 2 months, maximum). It is notable that, as shown for CDG compositions 3 and 4, neither methyl cellulose nor ethyl cellulose were able to prevent explosion from occurring, even with such a small sample size. The longer propyl side chains of the Methocel™ (hydromethyl propylcellulose) and Klucel™ (hydroxyl propylcellulose) were required to prevent explosion in the absence of the super absorbent. At 5 grams, all CDG compositions exploded immediately, regardless of the hydrophobic compound used.

TABLE 2. This Table shows the results of testing a 2-gram sample of a second group of non-conforming CDG compositions.

TABLE 2

NON-CONFORMING CDG COMPOSITION: No Hydrophobic Cmpd

| Super Absorbent | \multicolumn{6}{c}{CDG Composition} | | | | | |
|---|---|---|---|---|---|---|
| | 8 | 9 | 10 | 11 | 12 | 13 |
| Sodium Polyacrylate, 5,000 mol wt. | 20 | X | X | X | X | X |
| Sodium Polyacrylate, 11,000 mol wt. | X | 20 | X | X | X | X |
| Sodium polyacrylate, 20,000 mol wt. | X | X | 20 | X | X | X |
| Sodium polyacrylate, Diaper grade, gelation time 3 min. | X | X | X | 20 | X | X |
| Sodium polyacrylate, Liquid block grade, gelation time 30 min. | X | X | X | X | 20 | X |
| Potassium polyacrylate and polyacrylamide copolymer | X | X | X | X | X | 20 |
| Results | | | | | | |
| ClO$_2$ (wppm) | — | — | — | — | — | — |
| Explosion | Yes | Yes | Yes | Yes | Yes | Yes |

These compositions included the requisite active ingredients (for these compositions: sodium chlorite was 35 wt. pct and sodium hydrogen sulfate anhydrous was 45 wt pct). But only one of the required inert ingredients was present; in particular, only the super absorbent compound was present in the CDG compositions (i.e., the hydrophobic compound was absent).

All samples exploded at 2 grams, regardless of which particular super absorbent was used. This is because there was nothing to control the access of solvent to the active ingredients on initial contact with water. The super absorbent does not begin absorbing solvent for at least 30 to 60 seconds and, for these tests, no hydrophobic compound was present to repel water for that initial period of time.

TABLE 3. This table shows tests results for conforming CDG compositions.

TABLE 3

CONFORMING CDG COMPOSITION: 2-gram Samples

| Compound | \multicolumn{9}{c}{CDG Composition} | | | | | | | | |
|---|---|---|---|---|---|---|---|---|---|
| | 14 | 15 | 16 | 17 | 18 | 19 | 20 | 21 | 22 |
| Sodium Chlorite | 35 | 35 | 35 | 35 | 35 | 35 | 35 | 35 | 35 |
| Sodium Hydrogen sulfate anhydrous | 40 | 40 | 40 | 40 | 40 | 45 | 45 | 45 | 45 |
| Methyl cellulose | 15 | X | X | X | X | X | X | X | X |
| Methocel E15 | X | 15 | 15 | 15 | 15 | 12 | X | X | X |
| Methocel K100M | X | X | X | X | X | X | 12 | X | 12 |
| (Methocel J) | X | X | X | X | X | X | X | 12 | X |
| Sodium polyacrylate, 5,000 mol wt. | 10 | 10 | X | X | X | X | X | X | X |
| Sodium polyacrylate, <20,000 mol wt. | X | X | 10 | X | X | X | X | X | X |
| Sodium polyacrylate, Diaper grade, gelation time 3 min | X | X | X | 10 | X | X | X | X | X |
| Sodium polyacrylate, gelation time 30 min. | X | X | X | X | 10 | 8 | X | 8 | 8 |
| Potassium polyacrylate and polyacrylamide copolymer | X | X | X | X | X | X | 8 | X | X |
| Results | | | | | | | | | |
| ClO$_2$ (wppm) | 120 | 152 | 170 | 196 | 194 | 189 | 195 | 190 | 180 |
| Explosion | No | No | No | No | No | No | No | No | No |

Table 3 shows that with 2-gram samples, there were no explosions when the CDG composition was introduced to water. CDG compositions that included versions of Methocel™ as the hydrophobic compound showed good to excellent chlorine dioxide generation. CDG composition 14, which included methyl cellulose rather than a Methocel™ compound (HMPC) and low molecular weight sodium polyacrylate, generated predictably less chlorine dioxide than compositions 15-18. It is notable that the relatively higher-molecular-weight sodium polyacrylate of CDG composition 16 resulted in the generation of somewhat more chlorine dioxide than the relatively lower molecular weight sodium polyacrylate of CDG composition 15.

TABLE 4. This table shows the results of additional testing of conforming CDG compositions 14-22. In these tests, the sample weight was increased until explosion occurred, to a maximum of a 100-gram sample.

TABLE 4

CONFORMING CDG COMPOSITION-
Explosion vs. Sample Size

| Sample Weight | CDG Composition | | | | | | | | |
|---|---|---|---|---|---|---|---|---|---|
| | 14 | 15 | 16 | 17 | 18 | 19 | 20 | 21 | 22 |
| 5 grams | No | No | No | No | No | No | No | No | No |
| 10 grams | Yes | Yes | No | No | No | No | No | No | No |
| 25 grams | — | — | No | No | No | No | No | No | No |
| 50 grams | — | — | Yes | No | No | No | No | No | No |
| 100 grams | — | — | — | Yes | No | No | No | No | No |
| Shelf Life, months | 1 | 6 | | 36+ | 36+ | 36+ | 36+ | 36+ | 36+ |

Composition 14 shows that, similar to composition 3, CDG compositions using methyl cellulose as the hydrophobic compound are marginally effective. That is, explosion occurs at even small sample sizes. Composition 15 shows sodium polyacrylate with a mol wt of about 5,000 gm/mol is marginally effective. An increase in the concentration of the sodium polyacrylate would help somewhat in preventing explosion, but, as discussed later, such an increase will have a deleterious effect on chloride-dioxide generation.

Because the reaction proceeds quickly in CDG compositions 14-22, explosion is avoided even with the use of a quick-gelling super absorbent until a somewhat larger sample size (i.e., >50 grams) is tested. CDG compositions 17-22 proved to be very stable during storage. If properly packaged in a closed container, vacuum sealed bag, or canisters, etc., shelf life is in excess of 3 years.

TABLE 5

EFFECT OF SUPER ABSORBENT CONCENTRATION
ON $ClO_2$ YIELD

| | CDG Composition | | | |
|---|---|---|---|---|
| | 23 | 24 | 25 | 26 |
| Compound | | | | |
| Sodium Chlorite | 33 | 30 | 25 | 20 |
| Sodium Hydrogen sulfate anhydrous | 40 | 40 | 40 | 30 |
| Methocel ™ K100M | 15 | 12 | 10 | 10 |
| Sodium polyacrylate, gelation time 30 min. | 12 | 18 | 25 | 40 |
| Results | | | | |
| $ClO_2$ (wppm) | 160 | 142 | 68 | 12 |
| Explosion | No | No | No | No |
| Time to complete rxn | 3 hrs | 8 hrs | 24 hrs | 24 hrs |

Table 5 depicts the affect of increasing the composition of super absorbent compound on chlorine dioxide yield. For CDG compositions 23-26, the super absorbent compound is sodium polyacrylate with a 30 minute gelation time. As the concentration of super absorbent compound increases, chlorine dioxide yield decreases. Although there is variation in the concentration of the alkali metal chlorite compound and the hydrophobic compound for compositions 23-26 that would decrease chlorine dioxide generation, the decrease is more pronounced due to the increase in super absorbent compound. Based on these results and other testing, it is preferable that the amount of super absorbent compound in the CDG composition be limited to about 20 weight percent, and more preferably to a maximum of about 15 weight percent (unless a low yield of chlorine dioxide is desired)

TABLE 6. Table 6 shows the results of a one hour test of 2-gram and 50-gram samples of conforming CDG compositions having a low concentration of active ingredients. For these tests, the CDG compositions varied in terms of the concentration of the hydrophobic compound, the concentration and type of super absorbent, the presence of absence of surfactant.

TABLE 6

CONFORMING CDG COMPOSITION-
Low Concentration of Active Ingredients

| | CDG Composition | | | | | | | |
|---|---|---|---|---|---|---|---|---|
| Compound | 27 | 28 | 29 | 30 | 31 | 32 | 33 | 34 |
| Alkali Chlorite Salt | 5 | 5 | 5 | 5 | 5 | 5 | 5 | 5 |
| Acid | 10 | 10 | 10 | 10 | 10 | 10 | 10 | 10 |
| Methocel E15 | 5 | 5 | 5 | 5 | 15 | 15 | 15 | 15 |
| Sodium Polyacrylate, 5,000 mol wt | 4 | X | 4 | X | 10 | X | 10 | X |
| Sodium Polyacrylate, 50,000 mol wt | X | 4 | X | 4 | X | 10 | X | 10 |
| Surfactant | X | X | 20 | 20 | X | X | 20 | 20 |
| Inerts | Bal. | Bal. | Bal. | Bal. | Bal. | Bal. | Bal. | Bal. |
| Results | | | | | | | | |
| *$ClO_2$ (wppm) | 16 | 21 | 18 | 15 | 6 | 9 | 4 | 7 |
| **Explosion | No | No | No | No | No | No | No | No |

TABLE 7 below shows the results of a one hour test of 2-gram and 50-gram samples of conforming CDG compositions having a moderate concentration of active ingredients. For these tests, the CDG compositions varied in terms of the concentration of the hydrophobic compound and the concentration and type of super absorbent.

The data from Tables 6 and 7 show a reduction in chlorine dioxide yield as the concentration of sodium polyacrylate in the CDG composition increases, even at relatively low levels of sodium polyacrylate. That is, the increase from 4 wt pct to 10 wt pct of sodium polyacrylate decreases chlorine-dioxide yield substantially, at least on a percentage basis. There is a slight increase in chlorine dioxide yield as the concentration of Methocel in the CDG composition increases. Sodium polyacrylate has a significantly more pronounced affect on chlorine dioxide yield than Methocel™. The presence of the surfactant slightly depresses chlorine dioxide yield.

TABLE 7

CONFORMING CDG COMPOSITION-Moderate
Concentration of Active Ingredients

| | CDG Composition | | | | | | | |
|---|---|---|---|---|---|---|---|---|
| Compound | 35 | 36 | 37 | 38 | 39 | 40 | 41 | 42 |
| Alkali Chlorite Salt | 20 | 20 | 20 | 20 | 20 | 20 | 20 | 20 |
| Acid | 25 | 25 | 25 | 25 | 25 | 25 | 25 | 25 |
| Methocel E15 | 5 | 5 | 15 | 15 | 5 | 5 | 15 | 15 |

TABLE 7-continued

CONFORMING CDG COMPOSITION-Moderate Concentration of Active Ingredients

| | CDG Composition | | | | | | | |
|---|---|---|---|---|---|---|---|---|
| Compound | 35 | 36 | 37 | 38 | 39 | 40 | 41 | 42 |
| Sodium Polyacrylate, 5,000 mol wt | 4 | X | 4 | X | 10 | X | 10 | X |
| Sodium Polyacrylate, 50,000 mol wt | X | 4 | X | 4 | X | 10 | X | 10 |
| Surfactant | X | X | X | X | X | X | X | X |
| Inerts | Bal. | Bal. | Bal. | Bal. | Bal. | Bal. | Bal. | Bal. |
| Results | | | | | | | | |
| *$ClO_2$ (wppm) | 62 | 66 | 72 | 76 | 54 | 42 | 40 | 46 |
| **Explosion | Yes | No | No | No | No | No | No | No |

*Test results at 2 grams.
**Test results at 2 grams and 50 grams.
Inerts (which comprise the balance of each CDG composition), include sodium sulfate and sodium chloride in a 50:50 mixture).

TABLE 8. As previously disclosed, in some embodiments, CDG compositions in accordance with the present teachings include optional inert ingredients, such as surfactants for generating soapy solutions of chlorine dioxide. CDG compositions 43 and 44, which appear in Table 8, each include a surfactant for generating a soapy solution of chlorine dioxide.

For CDG composition 43, a 500 mg tablet was placed in one liter of water. For CDG composition 44, 2 grams of powder were placed in a canister that was then placed in one liter of water. The pH of the soapy solution resulting from CDG composition 44 was 6.5. The greater yield of chlorine dioxide for CDG composition 44 as compared to CDG composition 43 is a consequence of the use, in composition 43, of citric acid as the solid acid.

TABLE 8

CDG Composition with Surfactant

| | CDG Composition | |
|---|---|---|
| | 43 | 44 |
| Compound | | |
| Sodium Chlorite | 30 | 35 |
| Sodium Hydrogen sulfate anhydrous | — | 40 |
| Citric Acid | 40 | — |
| Methocel ™ E15 | 10 | 13 |
| Sodium Polyacrylate | 9 | 10 |
| Sodium Dodecyl Sulfate | 10 | 2 |
| Magnesium Stearate | 1 | — |
| Results | | |
| $ClO_2$ (wppm) | 36 | 186 |

CDG compositions in accordance with the present teachings will not, in preferred embodiments, include a free-chlorine source, such as sodium dichloroisocyanuric acid. But the addition of a free-chlorine source to the CDG compositions disclosed herein will not interfere with the chlorine-dioxide-generating reaction, nor will it increase the production of chlorine dioxide. To the extent that a free-chlorine source is present in a CDG composition in accordance with the present invention, it will enable a reduction in an active ingredient—the acid—, while maintaining the same maximum yield of chlorine dioxide (i.e., about 10 weight percent). In fact, a forty percent reduction in acid can be achieved while maintaining the same yield. As such, in some embodiments, the CDG composition will include a free-chlorine source. But regardless of whether a free-chlorine source is present in the CDG composition or not, the CDG composition must contain an appropriate quantity of a suitably selected hydrophobic compound and super absorbent or explosion will result.

TABLE 9. This Table depicts the results of testing conforming CDG compositions 16-22 for chlorine-dioxide gas generation. For these tests, the bottom of a canister that contained a CDG composition was immersed in solvent (liquid water). Chlorine dioxide that was generated was vented from the top of the canister to a confined volume (102 m$^3$) of air. The amount of chlorine dioxide released was measured by an Optex $ClO_2$ analyzer.

TABLE 9

CONFORMING CDG COMPOSITION-
$ClO_2$ Gas Generation Explosion vs. Sample Size

| | CDG Composition | | | | | | |
|---|---|---|---|---|---|---|---|
| Sample Weight | 45 | 46 | 47 | 48 | 49 | 50 | 51 |
| 2 grams | NO | NO | NO | NO | NO | NO | NO |
| 5 grams | NO | NO | NO | NO | NO | NO | NO |
| 10 grams | NO | NO | NO | NO | NO | NO | NO |
| 25 grams | NO | NO | NO | NO | NO | NO | NO |
| 50 grams | YES | YES | NO | NO | NO | NO | NO |
| 100 grams | — | — | NO | NO | NO | NO | NO |
| 200 grams | — | — | NO | NO | NO | NO | NO |

Chlorine dioxide began releasing from the canister within about 2 minutes and the concentration of chlorine dioxide in the volume peaked within about 30 minutes. In these tests, the weight of the CDG composition was increased until explosion occurred, to a maximum of a 200-gram sample. All CDG compositions tested for chlorine-dioxide-gas generation had a yield of about 0.1 g chlorine dioxide per gram of CDG composition.

Both CDG compositions 45 and 46 exploded above 25 grams. A relatively thicker layer of CDG composition in the canister is more likely to result in explosion. The thicker the layer, the more likely it is that the super absorbent, upon gelling, will trap chlorine dioxide gas, thereby resulting in an explosion. CDG compositions 47-51 did not explode in testing up to the sample size limit of 200 grams.

It is to be understood that the above-described embodiments are merely illustrative of the present invention and that many variations of the above-described embodiments can be devised by those skilled in the art without departing from the scope of the invention. It is therefore intended that such variations be included within the scope of the following claims and their equivalents.

What is claimed:

1. A dry blended composition for generating chlorine dioxide, comprising:
   (i) an alkali metal chlorite salt in an amount in a range of about 2 to about 35 weight percent;
   (ii) a solid acid source in an amount in a range of about 2 to about 40 weight percent;
   (iii) a hydrophobic compound, wherein the hydrophobic compound is sufficiently hydrophobic to repel solvent for at least 30 seconds, in an amount in a range of about 2 to about 60 weight percent; and (iv) a super absorbent compound, wherein the super absorbent compound is characterized by a gelation time of at least 5 minutes, in an amount in a range of about 2 to about 20 weight percent.

2. The composition of claim 1 and further wherein the maximum concentration of hydrophobic compound is about 20 weight percent.

3. The composition of claim 1 and further wherein the hydrophobic compound is selected from the group consisting of METHOCEL E15; METHOCEL E17; METHOCEL E19, METHOCEL H, METHOCEL J, METHOCEL K100 M, METHOCEL 310, KLUCEL 3, and KLUCEL 6.

4. The composition of claim 1 and further wherein the maximum concentration of the super absorbent compound is about 15 weight percent.

5. The composition of claim 1 and further wherein the maximum concentration of the super absorbent compound is about 10 weight percent.

6. The composition of claim 1 and further wherein the super absorbent is characterized by a gelation time of at least 30 minutes.

7. The composition of claim 1 and further wherein the super absorbent compound is selected from the group consisting of sodium polyacrylate having a molecular weight of at least 5000 gram/mol and sodium polyacrylamide having a molecular weight of at least 400 gram/mol.

8. The composition of claim 1 and further wherein the composition excludes both calcium salts and magnesium salts.

9. The composition of claim 1 and further wherein neither the alkali metal chlorite salt nor the solid acid source comprises a coating.

10. The composition of claim 1 and further wherein the composition excludes a source of free chlorine.

11. The composition of claim 1 and further comprising a surfactant.

12. The composition of claim 1 wherein the composition is selected from the group consisting of a more-preferred 5-percent CDG composition, a more-preferred 10-percent CDG composition, a more-preferred 20-percent CDG composition, a more-preferred 25-percent CDG composition, and a more-preferred 35-percent CDG composition.

13. A dry blended composition for generating chlorine dioxide, comprising:
   active ingredients in a quantity selected to result in a desired yield of chlorine dioxide;
   a hydrophobic compound, wherein the hydrophobic compound is sufficiently hydrophobic to repel solvent for at least 30 seconds, in an amount in a range of about 2 to about 60 weight percent; and
   a super absorbent compound characterized by:
   (a) a solvent-release property appropriate for the completion time of the chlorine-dioxide generating reaction; and
   (b) a gelation time appropriate for a completion time of the chlorine-dioxide generating reaction, wherein the gelation time is at least 5 minutes, wherein an amount o the super absorbent compound is in a range of about 2 to about 20 weight percent.

14. The composition of claim 13 wherein the composition excludes a free-chlorine source.

15. The composition of claim 13 wherein the composition excludes both calcium salts and magnesium salts.

16. A dry blended composition for generating chlorine dioxide, comprising:
   (i) an alkali metal chlorite salt in an amount of about 2 to about 70 weight percent;
   (ii) a solid acid source in an amount in a range of about 2 to about 80 weight percent;
   (iii) a hydrophobic compound, wherein the hydrophobic compound is sufficiently hydrophobic to repel solvent for at least 30 seconds, in an amount in a range of about 2 to about 60 weight percent; and
   (iv) a super absorbent compound, wherein the super absorbent compound is characterized by a gelation time of at least 5 minutes, in an amount of at least 2 weight percent up to a maximum amount, wherein the maximum amount is an amount that reduces a yield of chlorine dioxide by no more than about 20 percent from the highest yield of chlorine dioxide attainable from the composition, wherein the highest yield is attained at an amount of the super absorbent compound that is less than the maximum amount thereof.

17. The composition of claim 16 wherein the composition excludes a free-chlorine source.

18. The composition of claim 16 wherein the composition excludes both calcium salts and magnesium salts.

19. The composition of claim 16 wherein the alkali metal chlorite salt, the solid acid source, and the hydrophobic compound, and the super absorbent compound have an average particle size within the range of 50 mesh to 10 mesh.

20. The composition of claim 1, wherein the composition is stable for greater than one year.

\* \* \* \* \*